US012766318B2

(12) United States Patent
Carlson et al.

(10) Patent No.: US 12,766,318 B2
(45) Date of Patent: Oct. 20, 2026

(54) METHODS, SYSTEMS, AND APPARATUSES FOR COMBINED TUMOR TREATING FIELDS AND MENTAL HEALTH THERAPY

(71) Applicant: Novocure GMBH, Root (CH)

(72) Inventors: Kristen W. Carlson, Haifa (IL); Zeev Bomzon, Haifa (IL)

(73) Assignee: Novocure GMBH, Root (CH)

( * ) Notice: Subject to any disclaimer, the term of this patent is extended or adjusted under 35 U.S.C. 154(b) by 604 days.

(21) Appl. No.: 17/790,427

(22) PCT Filed: Dec. 21, 2020

(86) PCT No.: PCT/IB2020/001021
§ 371 (c)(1),
(2) Date: Jun. 30, 2022

(87) PCT Pub. No.: WO2021/136960
PCT Pub. Date: Jul. 8, 2021

(65) Prior Publication Data

US 2023/0147250 A1 May 11, 2023

Related U.S. Application Data

(60) Provisional application No. 62/955,744, filed on Dec. 31, 2019.

(51) Int. Cl.
*A61N 1/36* (2006.01)
*A61N 1/04* (2006.01)

(52) U.S. Cl.
CPC ....... *A61N 1/36002* (2017.08); *A61N 1/0476* (2013.01); *A61N 1/36025* (2013.01); *A61N 1/36034* (2017.08)

(58) Field of Classification Search
CPC .............. A61N 1/36002; A61N 1/0476; A61N 1/36025; A61N 1/36034; A61N 1/0456
See application file for complete search history.

(56) References Cited

U.S. PATENT DOCUMENTS 6,868,289 B2 * 3/2005 Palti ......................... A61N 1/40 607/76
7,565,205 B2 7/2009 Palti
9,186,505 B2 * 11/2015 Katsnelson ........ A61N 1/36025
(Continued)

FOREIGN PATENT DOCUMENTS

CN 102488967 A 6/2012
CN 109641130 A 4/2019
WO 2015/142922 A1 9/2015

OTHER PUBLICATIONS

Keyrouz, Shady & Caratelli, Diego. (2016). Dielectric Resonator Antennas: Basic Concepts, Design Guidelines, and Recent Developments at Millimeter-Wave Frequencies. International Journal of Antennas and Propagation. 2016. 1-20. 10.1155/2016/6075680. (Year: 2016).*

(Continued)

*Primary Examiner* — Jennifer Pitrak McDonald
*Assistant Examiner* — Christine Sison
(74) *Attorney, Agent, or Firm* — Ballard Spahr LLP

(57) ABSTRACT

Methods, systems, and apparatuses are described for using electrical stimulation to combine (e.g., concomitantly) tumor treating fields (TTFIelds) and mental health therapy (e.g., anti-depression therapy, anti-anxiety therapy, etc.).

14 Claims, 13 Drawing Sheets

(56) References Cited

U.S. PATENT DOCUMENTS

| | | | | |
|---|---|---|---|---|
| 9,662,492 | B1 * | 5/2017 | Tucker | A61B 5/053 |
| 2004/0068297 | A1 * | 4/2004 | Palti | A61N 1/18 607/2 |
| 2006/0167499 | A1 | 7/2006 | Palti | |
| 2006/0276858 | A1 * | 12/2006 | Palti | A61N 1/0408 607/76 |
| 2007/0225766 | A1 * | 9/2007 | Palti | A61N 1/40 607/2 |
| 2017/0014637 | A1 * | 1/2017 | Basser | A61N 1/40 |
| 2017/0281934 | A1 * | 10/2017 | Giladi | A61N 1/32 |
| 2019/0117956 | A1 | 4/2019 | Wenger et al. | |
| 2019/0314631 | A1 | 10/2019 | Wong et al. | |

OTHER PUBLICATIONS

Ballo M.T. et al., "Correlation of Tumor Treating Fields Dosimetry to Survival Outcomes in Newly Diagnose Glioblastoma: A Large-Scale Numerical Simulation-Based Analysis of Data from the Phase 3 EF-14 Randomized Trial," Int J Radiation Oncol Biol Phys, vol. 104, No. 5, 2019, pp. 1106-1113.

* cited by examiner

800
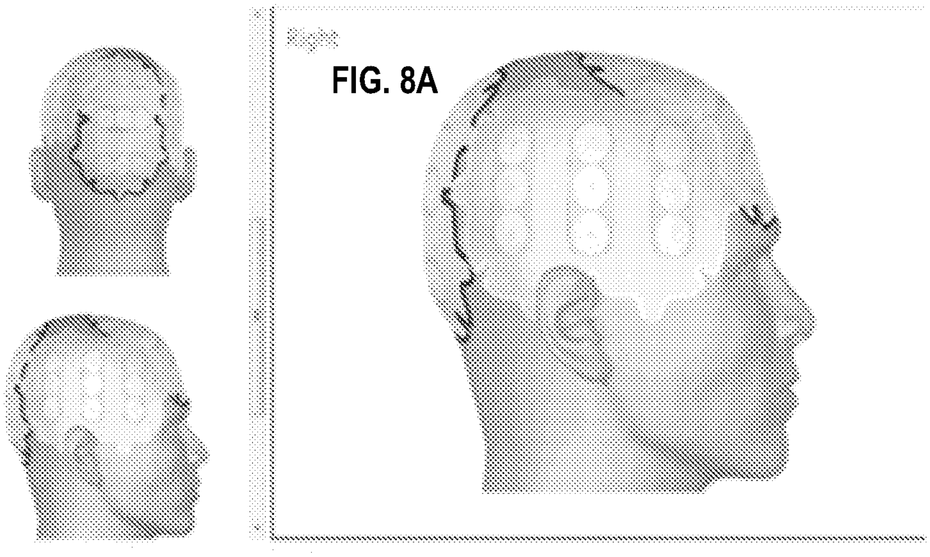
FIG. 8A
FIG. 8B
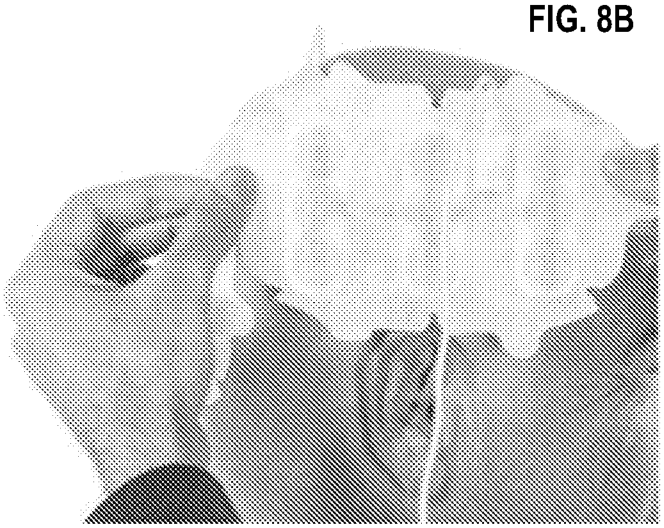

METHODS, SYSTEMS, AND APPARATUSES FOR COMBINED TUMOR TREATING FIELDS AND MENTAL HEALTH THERAPY

CROSS-REFERENCE TO RELATED APPLICATIONS

This application is a national stage filing under 35 U.S.C. § 371 of International Application No. PCT/US2020/01021, filed Dec. 21, 2020, which claims priority to U.S. Provisional Application No. 62/955,744, filed Dec. 31, 2019, which are herein incorporated by reference in their entireties.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma and approved combination therapy with chemotherapy for newly diagnosed patients. These electric fields are induced non-invasively by transducer arrays (i.e., arrays of electrodes) placed directly on the patient's scalp. TTFields also appear to be beneficial for treating tumors in other parts of the body. Patients, such as brain cancer patients, that benefit from TTFields therapy routinely experience depression, anxiety, cognitive decline, and/or other mental and/or neurological conditions. Low current and low frequency (e.g., less than 640 Hz, etc.) electrical stimulation may be used to treat depression, anxiety, cognitive decline, and/or other mental and/or neurological conditions, such as transcranially, called transcranial electric stimulation (TES), as shown by a growing body of TES empirical studies. Current and frequency requirements of TTFields therapy have not been empirically found to treat neurological conditions such as depression, anxiety, cognitive decline, and/or other mental and/or neurological conditions. For instance, the frequency of TTFields is too high to affect neural structures such as axons, dendrites, and neurons, and the amplitude of TTFields is higher than shown empirically to treat depression, anxiety, cognitive decline, and/or other mental and/or neurological conditions. However, the principle of superposition in linear electrical systems does not prohibit concomitant treatment with different waveforms via the same electrodes and/or via a separate set of electrodes through the same tissues, e.g., such concurrent transmission of electric currents at different frequencies will not necessarily interfere with each other. For TES, amplitude metrics refer to amperage supplied to the electrode in milliamps (mA) rather than field strength. Typically, mild currents in the range of 0.5-4.0 mA are effective to treat neurological and/or mental conditions such as depression, anxiety, and cognitive decline. The required amperage has been shown to be directly proportional to the thickness of a patient's skull. This is because the skull is the most electrically resistive tissue through which the current must flow to its target neural structures.

SUMMARY

Described are methods comprising causing cyclical application of a first electric field in a first direction via a first transducer array comprising a first plurality of electrodes and a second electric field in a second direction, opposite the first direction, via a second transducer array comprising a second plurality of electrodes, wherein the first electric field and the second electric field are at a first frequency, wherein each electrode of the first plurality of electrodes and each electrode of the second plurality of electrodes comprises a first material with a resonant frequency associated with the first frequency and a second material with a resonant frequency associated with a second frequency, and causing cyclical application of a third electric field in the first direction via the first plurality of electrodes and a fourth electric field in the second direction, via the second plurality of electrodes, wherein the third electric field and the fourth electric field are at the second frequency.

Also described are methods comprising causing, based on a time interval, cyclical application of a first electric field in a first direction via a first transducer array comprising a first plurality of electrodes and a second electric field in a second direction, opposite the first direction, via a second transducer array comprising a second plurality of electrodes, wherein the first electric field and the second electric field are at a first frequency, wherein each electrode of the first plurality of electrodes and each electrode of the second plurality of electrodes comprises a first material with a resonant frequency associated with the first frequency and a second material with a resonant frequency associated with a second frequency, and causing, based on the time interval, cyclical application of a third electric field in a third direction via a third transducer array comprising a third plurality of electrodes and a fourth electric field in a fourth direction, opposite the third direction, via a fourth transducer array comprising a fourth plurality of electrodes, wherein each electrode of the third plurality of electrodes and each electrode of the fourth plurality of electrodes comprises the first material with the resonant frequency associated with the first frequency and the second material with the resonant frequency associated with the second frequency, and wherein the third electric field and the fourth electric field are at the second frequency.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

FIG. 8A shows a three-dimensional array layout map 800.

FIG. 8B shows placement of tranducer arrays on the scalp of a patient.

DETAILED DESCRIPTION

Figure 1:
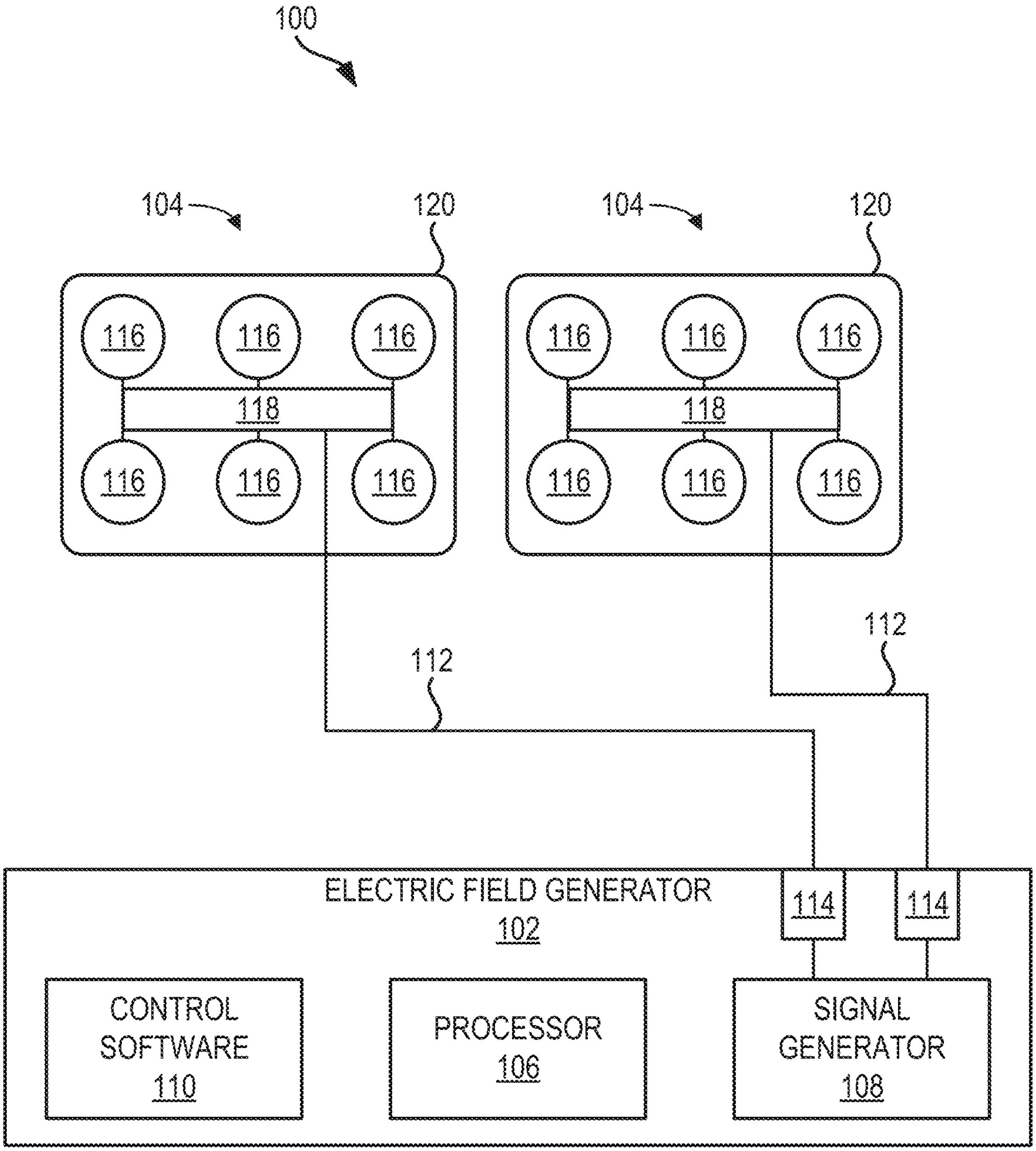
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

TTFields, also referred to herein as alternating electric fields, are established as an anti-mitotic cancer treatment modality because they interfere with proper microtubule assembly during metaphase and eventually destroy the cells during telophase and cytokinesis. The efficacy increases with increasing field strength and the optimal frequency are cancer cell line dependent with 200 kHz being the frequency for which inhibition of glioma cell growth caused by TTFields is highest. For cancer treatment, non-invasive devices were developed with capacitively coupled transducers that are placed directly at the skin region close to the tumor, for example, for patients with Glioblastoma Multiforme (GBM), the most common primary, malignant brain tumor in humans.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, one pair of transducer arrays may be located to the left and right (LR) of the tumor, and the other pair of transducer arrays may be located anterior and posterior (AP) to the tumor. Cycling the field between these two directions (i.e., LR and AP) ensures that a maximal range of cell orientations is targeted. Other positions of transducer arrays are contemplated beyond perpendicular fields. In an embodiment, asymmetric positioning of three transducer arrays is contemplated wherein one pair of the three transducer arrays may deliver alternating electric fields and then another pair of the three transducer arrays may deliver the alternating electric fields, and the remaining pair of the three transducer arrays may deliver the alternating electric fields.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible), measurements describing the geometry of the patient's head, tumor dimensions, and/or tumor location. Measurements used as input may be derived from imaging data. Imaging data is intended to include any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electric field distributes within the head as a function of the positions of the array and, in some aspects, take account for variations in the electrical property distributions within the heads of different patients.

FIG. 1 shows an example apparatus 100 for electrotherapeutic treatment. Generally, the apparatus 100 may be a portable, battery or power supply operated device which produces alternating electric fields within the body through non-invasive surface transducer arrays. The apparatus 100 may comprise an electric field generator 102 and one or more transducer arrays 104. The apparatus 100 may be configured to generate tumor treatment fields (TTFields) (e.g., at 150 kHz) via the electric field generator 102 and deliver the TTFields to an area of the body through the one or more transducer arrays 104. The electric field generator 102 may be a battery and/or power supply operated device. In an embodiment, the one or more transducer arrays 104 are uniformly shaped. In an embodiment, the one or more transducer arrays 104 are not uniformly shaped.

The electric field generator 102 may comprise a processor 106 in communication with a signal generator 108. The electric field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 kHz to about 500 kHz (preferably from about 100 kHz to about 300 kHz) (e.g., the TTFields). The voltages are such that the electric field intensity in tissue to be treated is in the range of about 0.1 V/cm to about 10 V/cm. For TES, amplitude metrics refer to amperage supplied to the electrode in milliamps (mA) rather than field strength. Typically, mild currents in the range of 0.5-4.0 mA are effective to treat neurological and/or mental conditions such as depression, anxiety, and cognitive decline. The required amperage has been shown to be directly proportional to the thickness of a patient's skull. This is because the skull is the most electrically resistive tissue through which the current must flow to its target neural structures.

One or more outputs 114 of the electric field generator 102 may be coupled to one or more conductive leads 112 that is attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and can be grounded to prevent the spread of the electric field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal to the signal generator 108 that causes the signal generator 108 to output the desired treatment frequency to the one or more transducer arrays 104.

The one or more transducer arrays 104 may be configured in a variety of shapes and positions to generate an electric field of the desired configuration, direction, and intensity at a target volume to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured to not come into direct contact with the skin as the electrodes 116 are separated from the skin by a layer of conductive hydrogel (not shown) (similar to that found on electrocardiogram pads).

The electrodes 116, the hydrogel, and the flexible circuit board 118 may be attached to a hypoallergenic medical adhesive bandage 120 to keep the one or more transducer arrays 104 in place on the body and in continuous direct contact with the skin. Each transducer array 104 may comprise one or more thermistors (not shown), for example, 8 thermistors, (accuracy ±1° C.) to measure skin temperature beneath the transducer arrays 104. The thermistors may be configured to measure skin temperature periodically, for example, every second. The thermistors may be read by the control software 110 while the TTFields are not being delivered to avoid any interference with the temperature measurements.

If the temperature measured is below a pre-set maximum temperature (Tmax), for example, 38.5-40.0° C.±0.3° C., between two subsequent measures, the control software 110 can increase current until the current reaches maximal treatment current (for example, 4 Amps peak-to-peak). If the temperature reaches Tmax+0.3° C. and continues to rise, the control software 110 can lower the current. If the temperature rises to 41° C., the control software 110 can shut off the TTFields therapy and an overheating alarm can be triggered.

Figure 2:
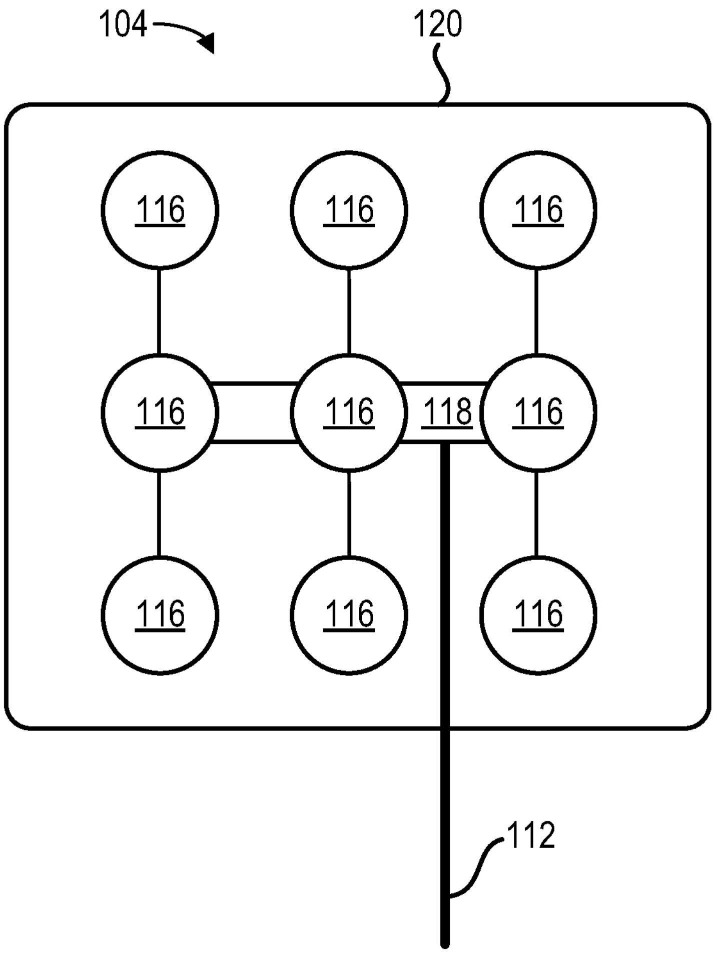
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

Alternative constructions for the one or more transducer arrays 104 are contemplated and may also be used, including, for example, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a subject/patient's body, with no insulating dielectric layer disposed between the conductive elements and the body. Other alternative constructions for implementing the transducer arrays may also be used. Any transducer array (or similar device/component) configuration, arrangement, type, and/or the like may be used for the methods and systems described herein as long as the transducer array (or similar device/component) configuration, arrangement, type, and/or the like is (a) capable of delivering TTFields to a subject/patient's body and (b) and may be positioned arranged, and/or placed on a portion of a patient/subject's body as described herein.

A status of the apparatus 100 and monitored parameters may be stored a memory (not shown) and can be transferred to a computing device over a wired or wireless connection. The apparatus 100 may comprise a display (not shown) for displaying visual indicators, such as, power on, treatment on, alarms, and low battery.

Figure 3A:
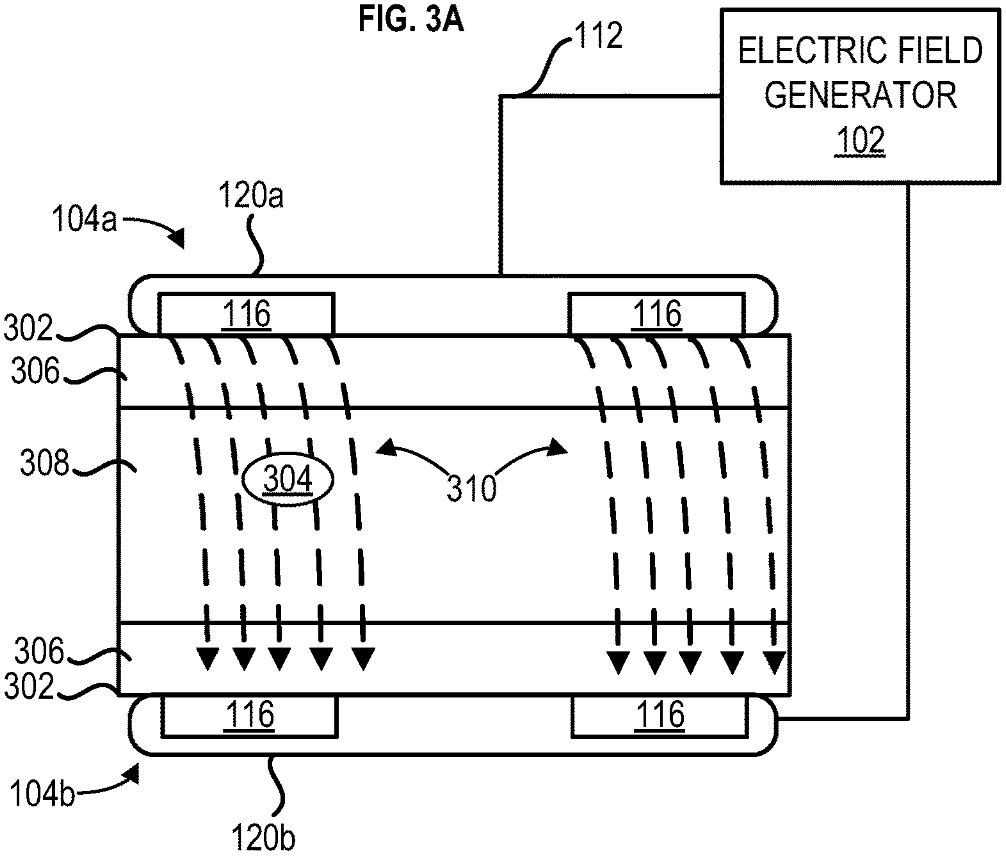
FIG. 3A and FIG. 3B illustrate an example application of the apparatus for electrotherapeutic treatment.
Figure 3B:
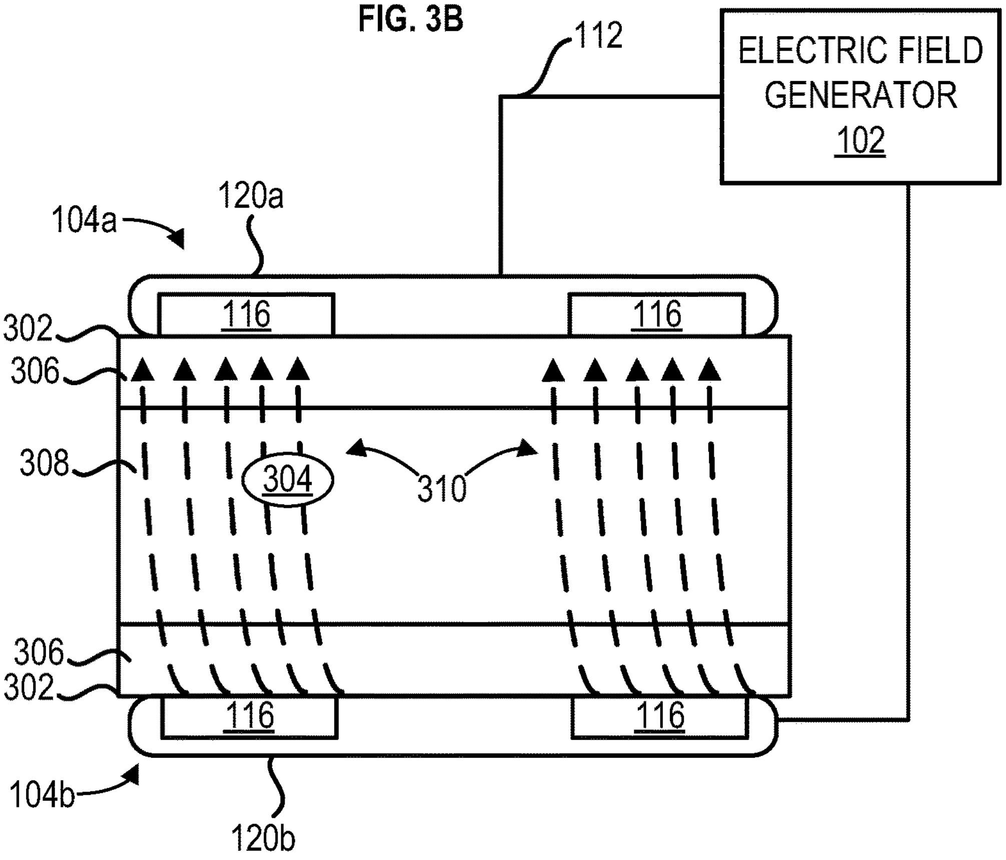

FIG. 3A and FIG. 3B illustrate an example application of the apparatus 100. A transducer array 104*a* and a transducer array 104*b* are shown, each incorporated into a hypoallergenic medical adhesive bandage 120*a* and 120*b*, respectively. The hypoallergenic medical adhesive bandages 120*a* and 120*b* are applied to skin surface 302. A tumor 304 is located below the skin surface 302 and bone tissue 306 and is located within brain tissue 308. The electric field generator 102 causes the transducer array 104*a* and the transducer array 104*b* to generate alternating electric fields 310 within the brain tissue 308 that disrupt rapid cell division exhibited by cancer cells of the tumor 304. The alternating electric fields 310 have been shown in non-clinical experiments to arrest the proliferation of tumor cells and/or to destroy them. Use of the alternating electric fields 310 takes advantage of the special characteristics, geometrical shape, and rate of dividing cancer cells, which make them susceptible to the effects of the alternating electric fields 310. The alternating electric fields 310 alter their polarity at an intermediate frequency (on the order of 100-300 kHz). The frequency used for a particular treatment may be specific to the cell type being treated (e.g., 150 kHz for MPM). The alternating electric fields 310 have been shown to disrupt mitotic spindle microtubule assembly and to lead to dielectrophoretic dislocation of intracellular macromolecules and organelles during cytokinesis. These processes lead to the physical disruption of the cell membrane and programmed cell death (apoptosis).

Because the effect of the alternating electric fields 310 is directional with cells dividing parallel to the field affected more than cells dividing in other directions, and because cells divide in all directions, alternating electric fields 310 may be delivered through two pairs of transducer arrays 104 that generate perpendicular fields within the treated tumor. More specifically, one pair of transducer arrays 104 may be located to the left and right (LR) of the tumor, and the other pair of transducer arrays 104 may be located anterior and posterior (AP) to the tumor. Cycling the alternating electric fields 310 between these two directions (e.g., LR and AP) ensures that a maximal range of cell orientations is targeted. In an embodiment, the alternating electric fields 310 may be delivered according to a symmetric setup of transducer arrays 104 (e.g., four total transducer arrays 104, two matched pairs). In another embodiment, the alternating electric fields 310 may be delivered according to an asymmetric setup of transducer arrays 104 (e.g., three total transducer arrays 104). An asymmetric setup of transducer arrays 104 may engage two of the three transducer arrays 104 to deliver the alternating electric fields 310 and then switch to another two of the three transducer arrays 104 to deliver the alternating electric fields 310, and the like.

In-vivo and in-vitro studies show that the efficacy of TTFields therapy increases as the intensity of the electric field increases. The methods, systems, and apparatuses described are configured for optimizing array placement on the patient's scalp to increase the intensity in the diseased region of the brain.

Figure 4A:
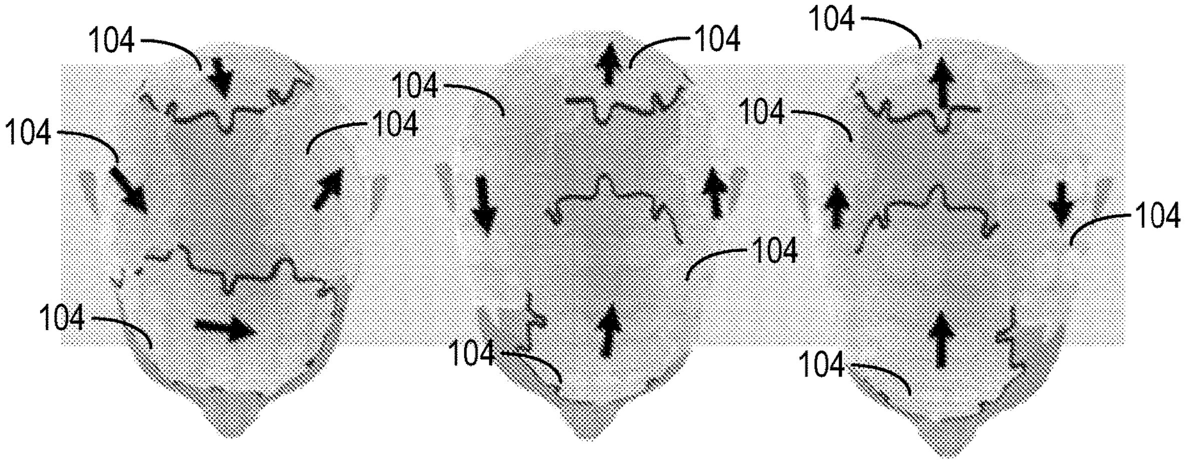
FIG. 4A shows transducer arrays placed on a patient's head.
Figure 4B:
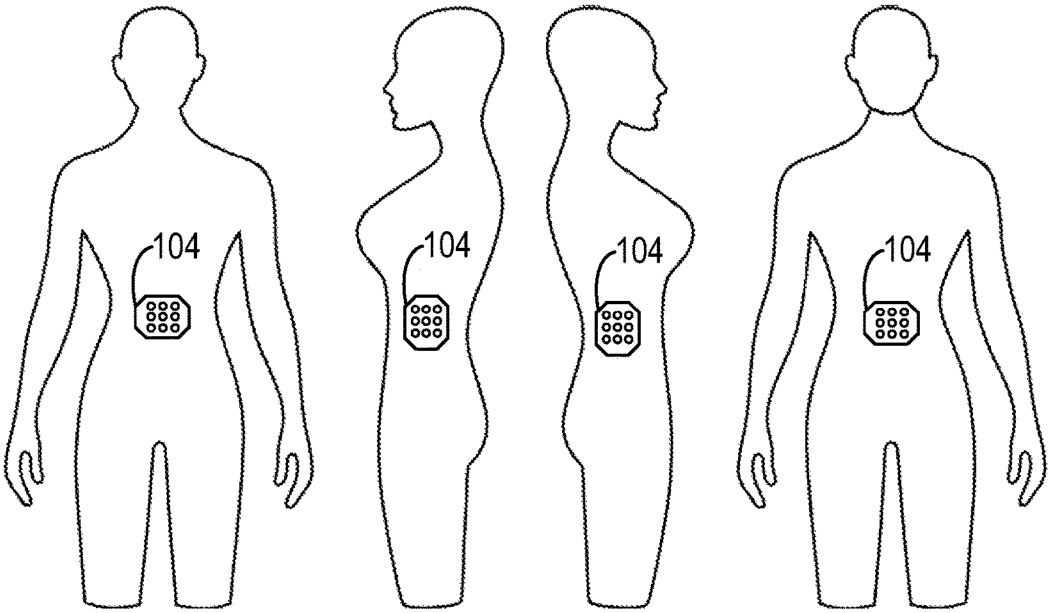
FIG. 4B shows transducer arrays placed on a patient's abdomen.
Figure 5A:
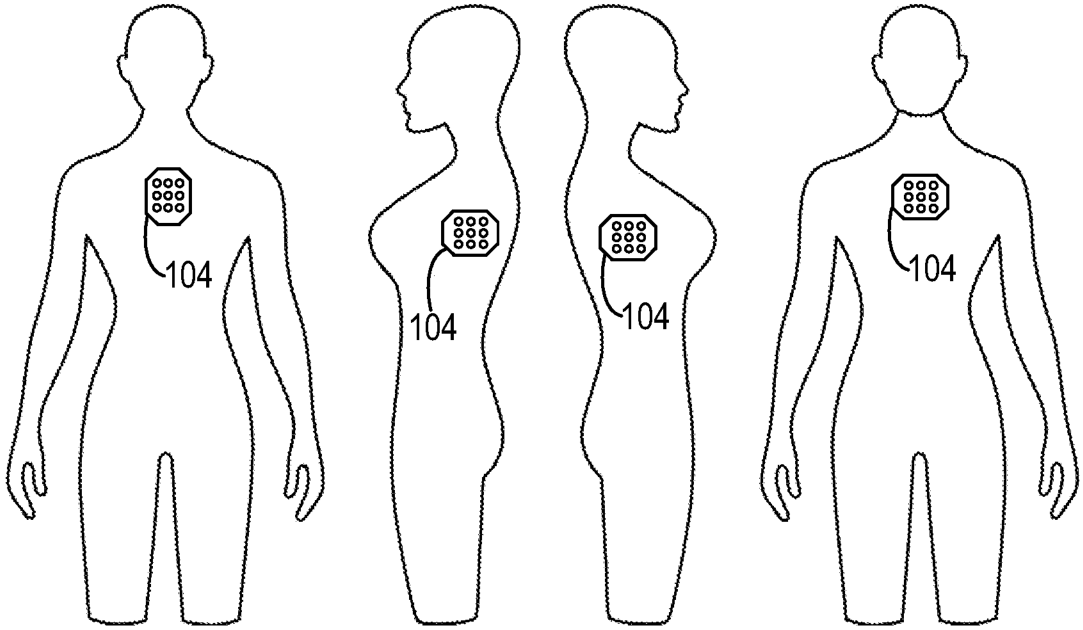
FIG. 5A, the transducer arrays placed on a patient's torso.
Figure 5B:
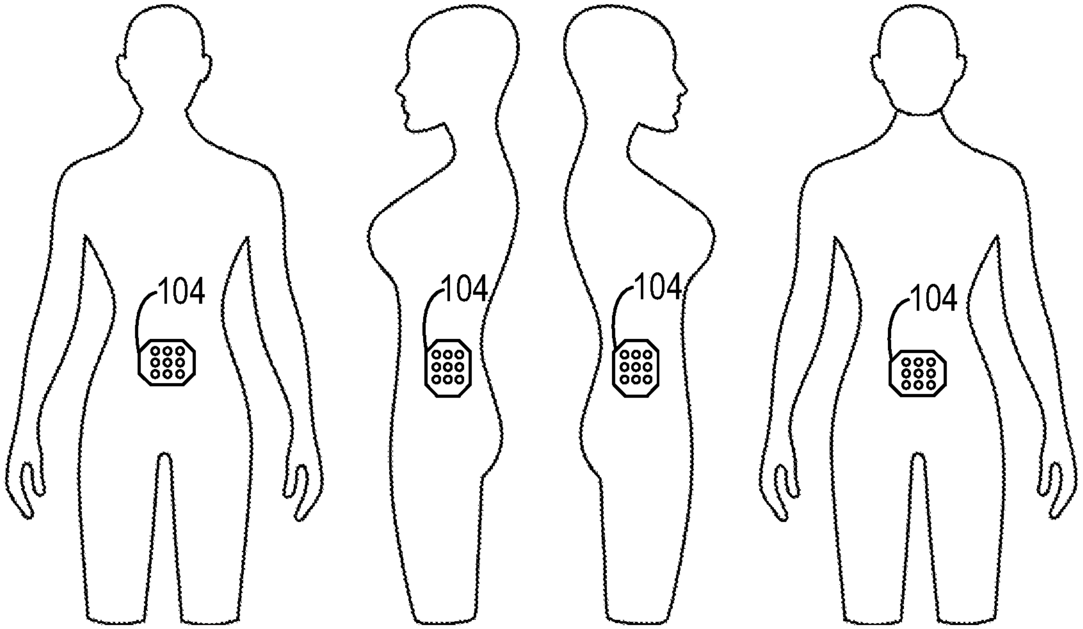
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) are specifically contemplated.

Figure 6:
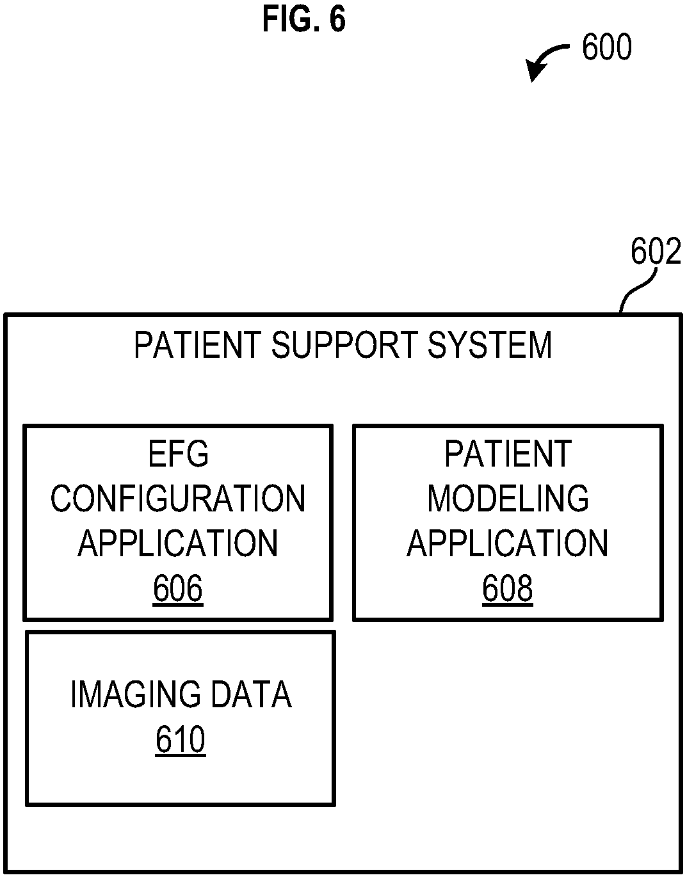
FIG. 6 is a block diagram depicting an electric field generator and a patient support system.

FIG. 6 is a block diagram depicting non-limiting examples of a system 600 comprising a patient support system 602. The patient support system 602 can comprise one or multiple computers configured to operate and/or store an electric field generator (EFG) configuration application 606, a patient modeling application 608, and/or imaging data 610. The patient support system 602 can comprise, for example, a computing device. The patient support system 602 can comprise, for example, a laptop computer, a desktop computer, a mobile phone (e.g., a smartphone), a tablet, and the like.

The patient modeling application 608 may be configured to generate a three dimensional model of a portion of a body of a patient (e.g., a patient model) according to the imaging data 610. The imaging data 610 may comprise any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electric field simulations.

To properly optimize array placement on a portion of a patient's body, the imaging data 610, such as MRI imaging data, may be analyzed by the patient modeling application 608 to identify a region of interest that comprises a tumor. In the context of a patient's head, to characterize how electric fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model to understand how an externally applied electric field, of preset frequency, will distribute throughout any portion of a patient's body, for example, the brain. The results of these simulations, employing paired array configurations, a constant current, and a preset frequency of 200 kHz, have demonstrated that electric field distributions are relatively non-uniform throughout the brain and that electric field intensities exceeding 1 V/cm are generated in most tissue compartments except CSF. Notably, for transcranial electric stimulation (TES), amplitude metrics refer to amperage supplied to the electrode in milliamps (mA) rather than field strength. Typically, mild currents in the range of 0.5-4.0 mA are effective to treat neurological and/or mental conditions such as depression, anxiety, and cognitive decline. The required amperage is directly proportional to the thickness of a patient's skull. This is because the skull is the most electrically resistive tissue through which the current must flow to its target neural structures.

Figure 7:
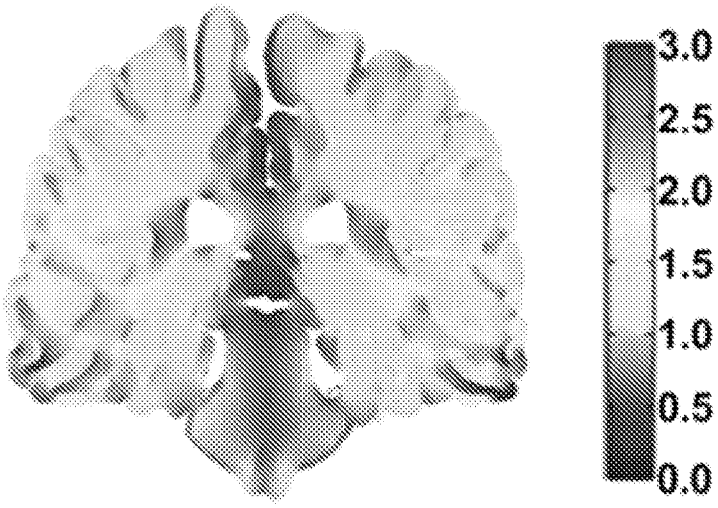
FIG. 7 illustrates electric field magnitude and distribution (in V/cm) shown in coronal view from a finite element method simulation model.

These results are obtained assuming total currents with a peak-to-peak value of 1800 milliamperes (mA) at the transducer array-scalp interface. This threshold of electric field intensity is sufficient to arrest cellular proliferation in glioblastoma cell lines. Additionally, by manipulating the configuration of paired transducer arrays, it is possible to achieve an almost tripling of electric field intensity to a particular region of the brain as shown in FIG. 7. FIG. 7 illustrates electric field magnitude and distribution (in V/cm) shown in the coronal view from a finite element method simulation model. This simulation employs a left-right paired transducer array configuration.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations and combinations of paired array layouts may be assessed to generate the configuration which delivers maximal electric field intensity to the tumor site. As shown in FIG. 8A, the output may be a three-dimensional array layout map 800. The three-dimensional array layout map 800 may be used by the patient and/or caregiver in arranging arrays on the scalp during the normal course of TTFields therapy as shown in FIG. 8B.

In an aspect, the patient modeling application 608 can be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques, or may be performed manually, for example by way of a physician.

Figure 9A:
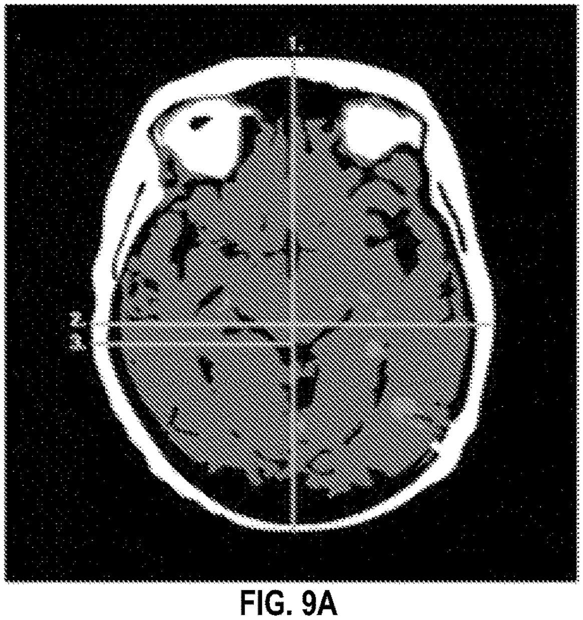
FIG. 9A shows an axial T1 sequence slice containing most apical image, including orbits used to measure head size.
Figure 9B:
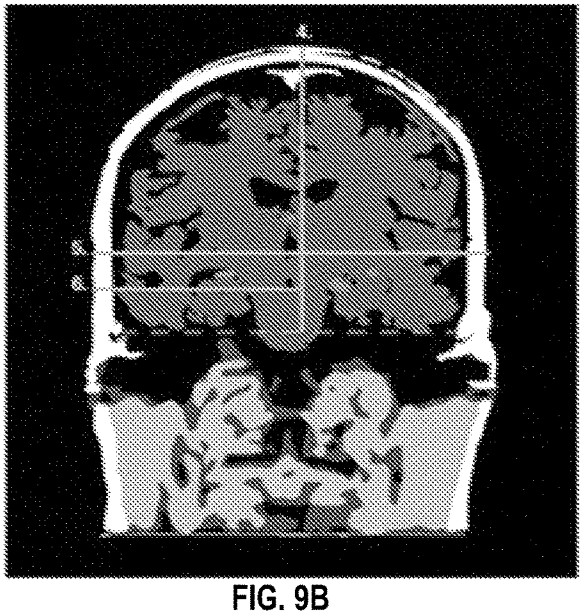
FIG. 9B shows a coronal T1 sequence slice selecting image at level of ear canal used to measure head size.
Figure 9C:
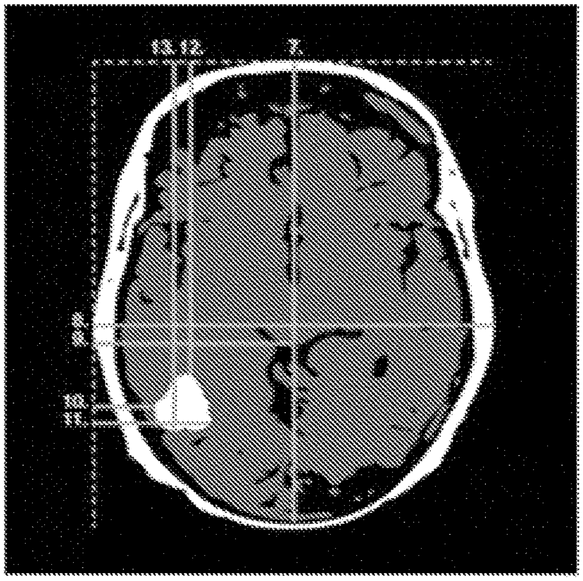
FIG. 9C shows a postcontrast T1 axial image shows maximal enhancing tumor diameter used to measure tumor location.
Figure 9D:
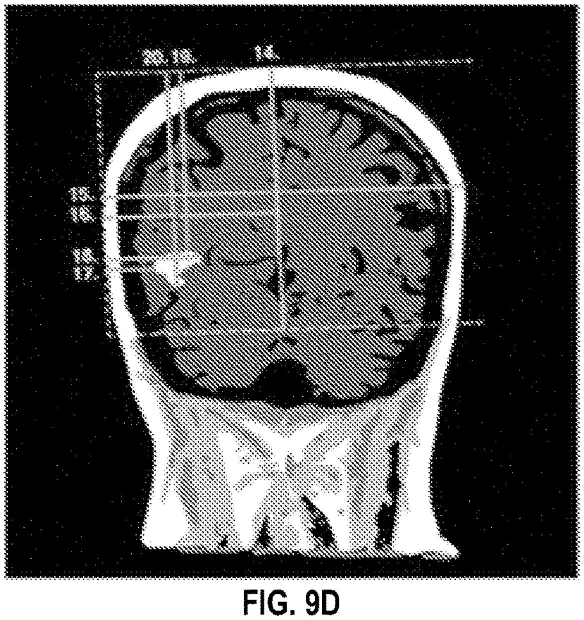
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right frontotemporal tumor, a right parieto-temporal tumor, a left frontotemporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing the most apical image, including orbits used to measure head size. FIG. 9B shows a coronal T1 sequence slice selecting image at the level of ear canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more of, head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as: a maximal anteroposterior (A-P) head size, commencing measurement from the outer margin of the scalp; a maximal width of the head perpendicular to the A-P measurement: right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the ear canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 post-contrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models can be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head into the template space, as well as the inverse transformation that maps the template into the patient space. The inverse transformation is applied to the 3D deformable template to yield an approximation of the patient's head in the absence of a tumor. Finally, the tumor (referred to as a region-of-interest (ROI)) is planted back into the deformed template to yield the full patient model. The patient model may be a digital representation in three-dimensional space of the portion of the patient's body, including internal structures, such as tissues, organs, tumors, etc.

TABLE 1

| Tissue Type | Conductivity, S/m | Relative Permittivity |
|---|---|---|
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |
| Necrotic tumor | 1 | 110 |
| Hematoma | 0.3 | 2000 |
| Ischemia | 0.18 | 2500 |
| Atrophy | 1 | 110 |
| Air | 0 | 0 |

Delivery of TTFields may then be simulated by the patient modeling application 608 using the patient model. Simulated electric field distributions, dosimetry, and simulation-based analysis are described in U.S. Patent Publication No. 20190117956 A1 and Publication "Correlation of Tumor treating Fields Dosimetry to Survival Outcomes in Newly Diagnosed Glioblastoma: A Large-Scale Numerical Simulation-based Analysis of Data from the Phase 3 EF-14 randomized Trial" by Ballo, et al. (2019) which are incorporated herein by reference in their entirety.

To ensure systematic positioning of the transducer arrays relative to the tumor location, a reference coordinate system may be defined. For example, a transversal plane may initially be defined by conventional LR and AP positioning of the transducer arrays. The left-right direction may be defined as the x-axis, the AP direction may be defined as the y-axis, and the craniocaudal direction normal to the XY-plane may be defined as the Z-axis.

After defining the coordinate system, transducer arrays may be virtually placed on the patient model with their centers and longitudinal axes in the XY-plane. A pair of transducer arrays may be systematically rotated around the z-axis of the head model, i.e. in the XY-plane, from 0 to 180 degrees, thereby covering the entire circumference of the head (by symmetry). The rotation interval may be, for example, 15 degrees, corresponding to approximately 2 cm translations, giving a total of twelve different positions in the range of 180 degrees. Other rotation intervals are contemplated. Electric field distribution calculations may be performed for each transducer array position relative to tumor coordinates.

Electric field distribution in the patient model may be determined by the patient modeling application 608 using a finite element (FE) approximation of electrical potential. In general, the quantities defining a time-varying electromagnetic field are given by the complex Maxwell equations. However, in biological tissues and at the low to intermediate frequency of TTFields (f=200 kHz), the electromagnetic wavelength is much larger than the size of the head and the electric permittivity $\varepsilon$ is negligible compared to the real-valued electric conductivity $\sigma$, i.e., where $\omega=2\pi f$ is the angular frequency. This implies that the electromagnetic propagation effects and capacitive effects in the tissue are negligible, so the scalar electric potential may be well approximated by the static Laplace equation $\nabla\cdot(\sigma\nabla\phi)=0$, with appropriate boundary conditions at the electrodes and skin. Thus, the complex impedance is treated as resistive (i.e. reactance is negligible) and currents flowing within the volume conductor are, therefore, mainly free (Ohmic) currents. The FE approximation of Laplace's equation was calculated using the SimNIBS software (simnibs.org). Computations were based on the Galerkin method and the residuals for the conjugate gradient solver were required to be <1E-9. Dirichlet boundary conditions were used with the electric potential was set to (arbitrarily chosen) fixed values at each set of electrode arrays. The electric (vector) field was calculated as the numerical gradient of the electric potential and the current density (vector field) was computed from the electric field using Ohm's law. The potential difference of the electric field values and the current densities were linearly rescaled to ensure a total peak-to-peak amplitude for each array pair of 1.8 A, calculated as the (numerical) surface integral of the normal current density components over all triangular surface elements on the active electrode discs. This corresponds to the current level used for clinical TTFields therapy by the Optune® device. The "dose" of TTFields was calculated as the intensity (L2 norm) of the field vectors. The modeled current is assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electric field strength generated by transducer arrays placed at multiple locations on the patient may be determined by the patient modeling application 608 for one or more tissue types. In an aspect, the transducer array position that corresponds to the highest average electric field strength in the tumor tissue type(s) may be selected as a desired (e.g., optimal) transducer array position for the patient. In another aspect, one or more candidate positions for a transducer array(s) may be excluded as a result of a physical condition of the patient. For example, one or more candidate positions may be excluded based on areas of skin irritation, scars, surgical sites, discomfort, etc. Accordingly, the transducer array position that corresponds to the highest average electric field strength in the tumor tissue type(s), after excluding one or more candidate positions, may be selected as a desired (e.g., optimal) transducer array position for the patient. Thus, a transducer array position may be selected that results in less than the maximum possible average electric field strength.

The patient model may be modified to include an indication of the desired transducer array position. The resulting patient model, comprising the indication(s) of the desired transducer array position(s), may be referred to as the three-dimensional array layout map (e.g., three-dimensional array layout map 600). The three-dimensional array layout map may thus comprise a digital representation, in three-dimensional space, of the portion of the patient's body, an indication of tumor location, an indication of a position for placement of one or more transducer arrays, combinations thereof, and the like.

The three-dimensional array layout map may be provided to the patient in a digital form and/or a physical form. The patient, and/or a patient caregiver, may use the three-dimensional array layout map to affix one or more transducer arrays to an associated portion of the patient's body (e.g., head).

As described, transducer arrays affixed to a patient's head according to a three-dimensional array layout map may be used to treat a tumor in the brain of the patient, such as a patient with Glioblastoma Multiforme (GBM), the most common primary, malignant brain tumor in humans. In some instances, patients that undergo TTFields treatment for GBM may be affected by depression, anxiety, cognitive decline, and/or other mental and/or neurological conditions. The devices/components described herein (e.g., the electric field generator 102, the EFG configuration application 606, etc.) may be configured to treat depression, anxiety, cognitive decline, and/or other mental and/or neurological conditions. In some instances, transducer arrays may be configured to deliver transcranial electric stimulation (TES) to a patient to treat a wide variety of neurological conditions, including depression (e.g., major depressive disorder (MDD), etc.), addiction, stroke after-effects, cognitive enhancement, and/or the like. Further, in the case of emotional depression, such depression may deleteriously impair the patient's immune system, which in turn will reduce the patient's ability to control tumor growth due to inherent immune system anti-tumoral effects or immune system anti-tumor effects that are enhanced by TTFields. Further, patients with brain cancer (e.g. GBM) are likely to experience anxiety about their condition. Further, GBM is an age-related disease, and thus its prevalence increases with age, such as in patients over age 50 years, who are also more likely to experience normal, age-related cognitive decline. To provide TES treatment, the devices/components described herein (e.g., the electric field generator 102, the EFG configuration application 606, etc.) may be configured to generate and/or apply direct current or low-frequency alternating current, at random frequencies, from 0 Hz to 640 Hz. In some instances, a TES device (e.g., a TES circuit, a TES component, a signal generator, etc.) may be in communication with the devices/components described herein (e.g., the electric field generator 102, the EFG configuration application 606, etc.) and may generate, provide, manage, apply, and/or the like direct current or low-frequency alternating current, at random frequencies, from 0 Hz to 640 Hz. In some instances, the devices/components described herein (e.g., the electric field generator 102, the EFG configuration application 606, etc.) may be configured with and/or include the TES device. In some instances, the devices/components described herein (e.g., the electric field generator 102, the EFG configuration application 606, etc.) may be separate from the TES device. In some instances, the devices/components described herein (e.g., the electric field generator 102, the EFG configuration application 606, etc.) may generate provide, manage, apply, and/or the like TTFields, and the TES device may generate, provide, manage, apply, and/or the like direct current or low-frequency alternating current, at random frequencies, from 0 Hz to 640 Hz, based on a time interval, cycle, rotation, exchange, and/or the like.

In some instances, optimal positions for one or more transducer arrays intermittently distributing electric fields at varying frequencies and power levels that concomitant treatment brain cancer (e.g., GBM, etc.) and mental depression, anxiety, cognitive decline, and other neurological conditions may be determined, and the one or more transducer arrays may include materials with resonant frequencies that effectively deliver the electric fields at varying frequencies and power levels that concomitant treatment brain cancer (e.g., GBM, etc.) and mental depression, anxiety, cognitive decline, and other neurological conditions. Such optimal positions for TES are specified according to standard montage nomenclature covering the cranial lobes (frontal, parietal, temporal, central, and occipital) along with the hemisphere (right or left) of the lobe, which are easily translated to TTFields electrode position. Different combinations of montage specification have been empirically proven to optimally treat different mental or neurological disorders or conditions. For example, electrodes near the dorsolateral prefrontal cortex may be optimally placed to treat cognitive decline.

Regarding electrode material composition, the one or more transducer arrays may include electrodes constructed of a material, such as ceramic, with a resonant frequency that is associated with electric fields ranging from 50 to 500 kHz (e.g., a frequency range associated with treating GBM and/or the like), and electrodes constructed of a material, such as rubber, with a resonant frequency that is associated with electric fields of less than 640 Hz (e.g., a frequency range associated with treating MDD and/or the like). Electrodes, based on their material composition and applied frequency, may reduce edge effects where excessive current is present in 'hot spots', and ultimately improving the patient experience.

Figure 10A:
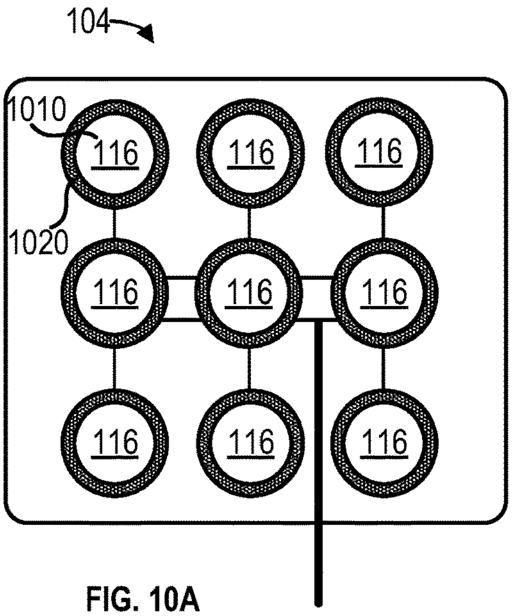
FIG. 10A shows an example transducer array for combined tumor treating fields and mental health therapy.

FIG. 10A illustrates the one or more transducer arrays 104 as described in FIG. 1. The one or more transducer arrays 104 arrays may comprise one or more electrodes 116. The one or more electrodes 116 may be made from a first material 1010, such as ceramic or any other any material, with a high dielectric constant and/or a resonant frequency associated with the frequency range for TTFields therapy. The one or more electrodes 116 may be made from a second material 1020, such as rubber or any other any material, with a low dielectric constant and/or a resonant frequency associated with the frequency range for transcranial electric stimulation (TES) to treat MDD and/or other mental and/or neurological conditions. In some instances, the second material 1020 may surround the first material 1010.

Figure 10B:
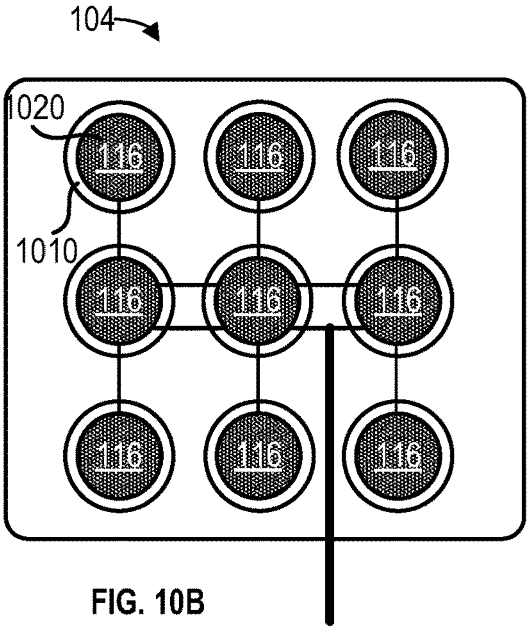
FIG. 10B shows an example transducer array for combined tumor treating fields and mental health therapy.

FIG. 10B illustrates the one or more transducer arrays 104 as described in FIG. 1. The one or more transducer arrays 104 arrays may comprise one or more electrodes 116. The one or more electrodes 116 may be made from a first material 1010, such as ceramic or any other any material, with a high dielectric constant and/or a resonant frequency associated with the frequency range for TTFields therapy. The one or more electrodes 116 may be made from a second material 1020, such as rubber or any other any material, with a low dielectric constant and/or a resonant frequency associated with the frequency range for transcranial electric stimulation (TES) to treat MDD and/or other mental and/or neurological conditions. In some instances, the first material 1010 may surround the second material 1020.

Figure 10C:
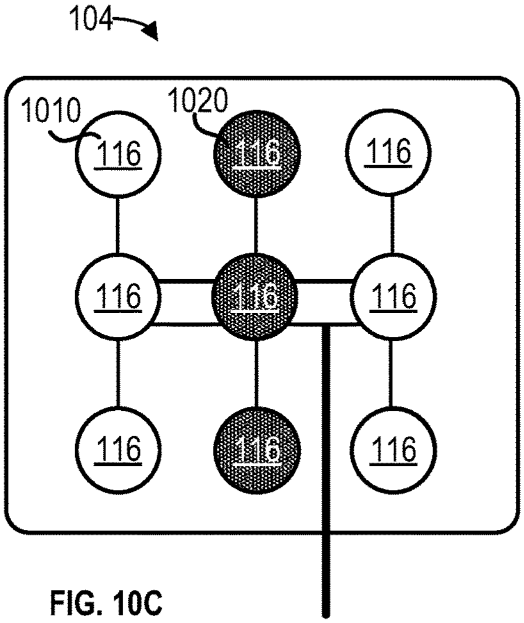
FIG. 10C shows an example transducer array for combined tumor treating fields and mental health therapy.

FIG. 10C illustrates the one or more transducer arrays 104 as described in FIG. 1. The one or more transducer arrays 104 arrays may comprise one or more electrodes 116. Some of the one or more electrodes 116 may be made from a first material 1010, such as ceramic or any other any material, with a high dielectric constant and/or a resonant frequency associated with the frequency range for TTFields therapy (e.g., 50 kHz to about 500 kHz, etc.). Some of the one or more electrodes 116 may be made from a second material 1020, such as rubber or any other any material, with a low dielectric constant and/or a resonant frequency associated with the frequency range for transcranial electric stimulation (TES) to treat MDD and/or other mental and/or neurological conditions (e.g., 0 Hz to 640 Hz, etc.). Any arrangement and/or material configuration of the one or more electrodes 116 should be appreciated and enabled by the present disclosure.

The signal generator 108 (FIG. 1) may generate one or more electric signals in the shape of waveforms or trains of pulses. The signal generator 108 may be configured to generate an alternating voltage waveform at frequencies in the range from about 50 kHz to about 500 kHz (preferably from about 100 kHz to about 300 kHz) (e.g., the TTFields). The voltages are such that the electric field intensity in tissue to be treated is in the range of about 0.1 V/cm to about 10 V/cm. Notably, for transcranial electric stimulation (TES), amplitude metrics refer to amperage supplied to the electrode in milliamps (mA) rather than field strength. Typically, mild currents in the range of 0.5-4.0 mA are effective to treat neurological and/or mental conditions such as depression, anxiety, and cognitive decline. The required amperage is directly proportional to the thickness of a patient's skull. This is because the skull is the most electrically resistive tissue through which the current must flow to its target neural structures.

The signal generator 108 may be configured to generate an alternating voltage waveform at frequencies in the range from 0 to about 640 Hz (e.g., for TES), with current ranging from 1-2 mA. The signal generator 108 may alternate, based on a time interval, between generating an alternating voltage waveform at frequencies in the range from about 50 kHz to about 500 kHz, and generating an alternating voltage waveform at frequencies in the range from 0 to about 640 Hz. Alternating, based on a time interval, between generating an alternating voltage waveform at frequencies in the range from about 50 kHz to about 500 kHz, and generating an alternating voltage waveform at frequencies in the range from 0 to about 640 Hz enables allows concomitant treatment of GBM and MDD without crosstalk interference effects.

Figure 11:
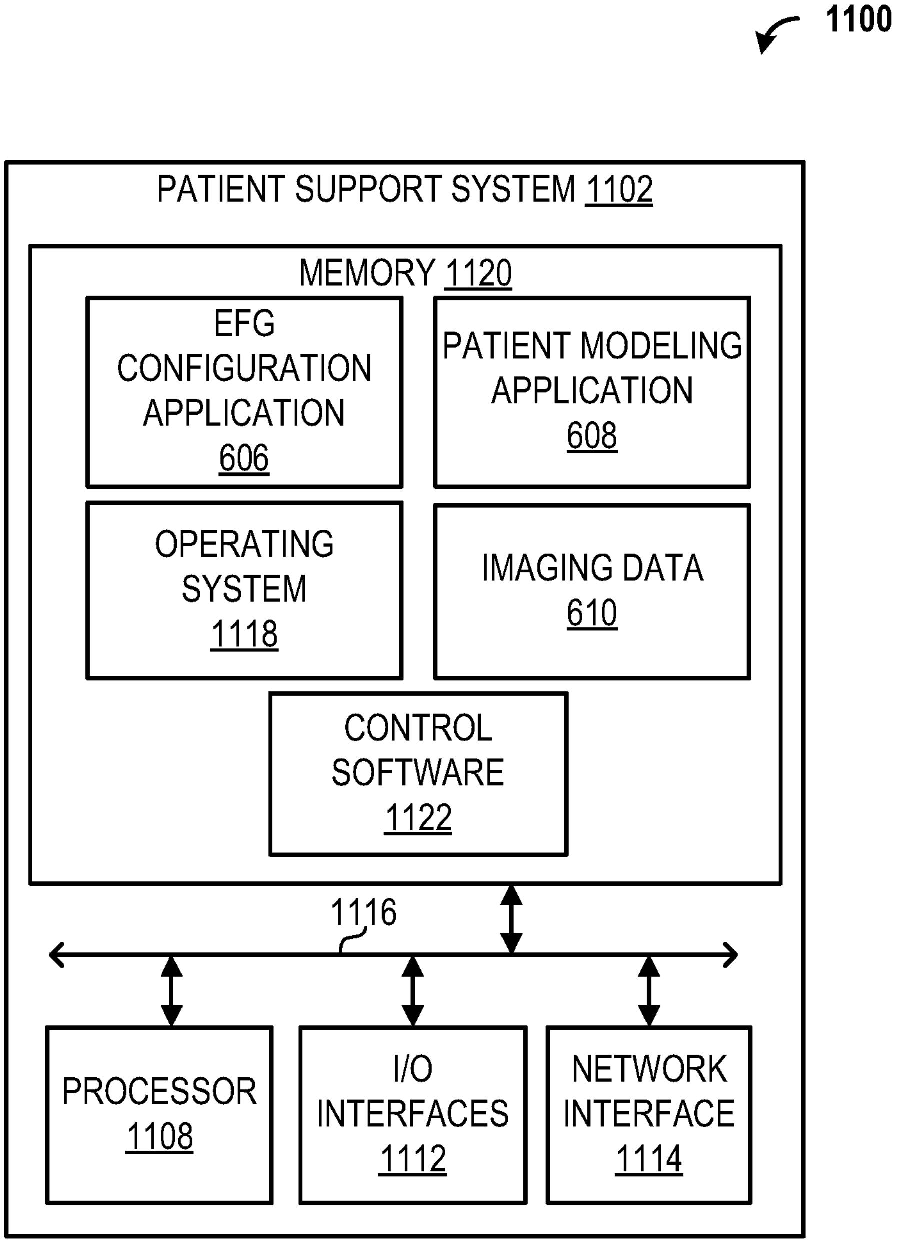
FIG. 11 is a block diagram depicting an example operating environment.

FIG. 11 is a block diagram depicting an environment 1100 comprising a non-limiting example of a patient support system 1102. In an aspect, some or all steps of any described method may be performed on a computing device as described herein. The patient support system 1102 can comprise one or multiple computers configured to store one or more of the EFG configuration application 606, the patient modeling application 608, the imaging data 610, and the like.

The patient support system 1102 can be a digital computer that, in terms of hardware architecture, generally includes a processor 1108, memory system 1110, input/output (I/O) interfaces 1112, and network interfaces 1114. These components (608, 610, 1112, and 1114) are communicatively coupled via a local interface 1116. The local interface 1116 can be, for example, but not limited to, one or more buses or other wired or wireless connections, as is known in the art. The local interface 1116 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1108 can be a hardware device for executing software, particularly that stored in memory system 1110. The processor 1108 can be any custom made or commercially available processor, a central processing unit (CPU), an auxiliary processor among several processors associated with the patient support system 1102, a semiconductor-based microprocessor (in the form of a microchip or chipset), or generally any device for executing software instructions. When the patient support system 1102 is in operation, the processor 1108 can be configured to execute software stored within the memory system 1110, to communicate data to and from the memory system 1110, and to generally control operations of the patient support system 1102 pursuant to the software.

The I/O interfaces 1112 can be used to receive user input from and/or for providing system output to one or more devices or components. User input can be provided via, for example, a keyboard and/or a mouse. System output can be provided via a display device and a printer (not shown). I/O interfaces 1112 can include, for example, a serial port, a parallel port, a Small Computer System Interface (SCSI), an IR interface, an RF interface, and/or a universal serial bus (USB) interface.

The network interface 1114 can be used to transmit and receive from the patient support system 104. The network interface 1114 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1114 may include address, control, and/or data connections to enable appropriate communications.

The memory system 1110 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1110 may incorporate electronic, magnetic, optical, and/or other types of storage media. Note that the memory system 1110 can have a distributed architecture, where various components are situated remote from one another, but can be accessed by the processor 1108.

The software in memory system 1110 may include one or more software programs, each of which comprises an ordered listing of executable instructions for implementing logical functions. In the example of FIG. 11, the software in the memory system 1110 of the patient support system 1102 can comprise the EFG configuration application 606, the patient modeling application 608, the imaging data 610, and a suitable operating system (O/S) 1118. The operating system 1118 essentially controls the execution of other computer programs, and provides scheduling, input-output control, file and data management, memory management, and communication control, and related services.

For purposes of illustration, application programs and other executable program components such as the operating system 1118 are illustrated herein as discrete blocks, although it is recognized that such programs and components can reside at various times in different storage components of the patient support system 104. An implementation of the EFG configuration application 606, the patient modeling application 608, the imaging data 610, and/or the control software 110 can be stored on or transmitted across some form of computer-readable media. Any of the disclosed methods can be performed by computer readable instructions embodied on computer-readable media. Computer-readable media can be any available media that can be accessed by a computer. By way of example and not meant to be limiting, computer-readable media can comprise "computer storage media" and "communications media." "Computer storage media" can comprise volatile and non-volatile, removable and non-removable media implemented in any methods or technology for storage of information such as computer-readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Figure 12:
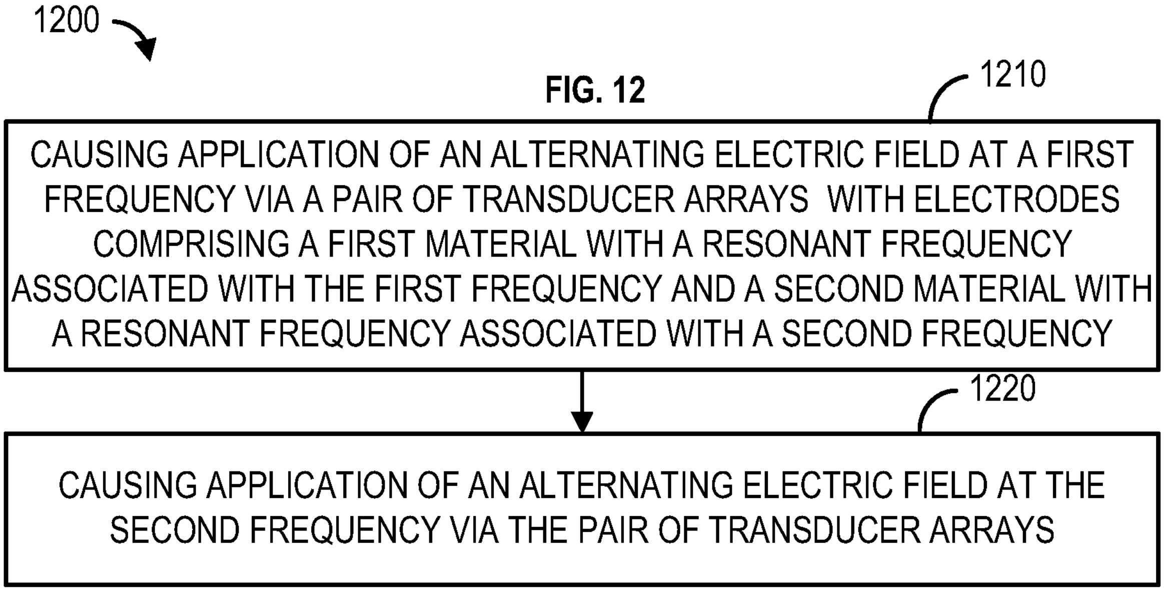
FIG. 12 shows an example method.

In an embodiment, illustrated in FIG. 12, one or more of the apparatus 100, the patient support system 602, the patient modeling application 608, and/any other device/component described herein can be configured to perform a method 1200 comprising, at 1210, causing cyclical application of a first electric field in a first direction via a first transducer array comprising a first plurality of electrodes and a second electric field in a second direction, opposite the first direction, via a second transducer array comprising a second plurality of electrodes, wherein the first electric field and the second electric field are at a first frequency, wherein each electrode of the first plurality of electrodes and each electrode of the second plurality of electrodes comprises a first material with a resonant frequency associated with the first frequency and a second material with a resonant frequency associated with a second frequency.

At 1220, causing cyclical application of a third electric field in the first direction via the first plurality of electrodes and a fourth electric field in the second direction, via the second plurality of electrodes, wherein the third electric field and the fourth electric field are at the second frequency.

In some instances, the first frequency may include a frequency between 50 and 500 kHz, and the first electric field and the second electric field each comprise an electric field strength of at least 1 V/cm, and the second frequency may include a frequency of less than 640 Hz. Notably, for transcranial electric stimulation (TES), amplitude metrics refer to amperage supplied to the electrode in milliamps (mA) rather than field strength. Typically, mild currents in the range of 0.5-4.0 mA are effective to treat neurological and/or mental conditions such as depression, anxiety, and cognitive decline. The required amperage is directly proportional to the thickness of a patient's skull. This is because the skull is the most electrically resistive tissue through which the current must flow to its target neural structures.

In some instances, the first material may include and/or be ceramic and the second material may include and/or be rubber. In some instances, based on the first frequency, the cyclical application of the first electric field and the second electric field treats a tumor within the brain of a subject, and wherein, based on the second frequency, the cyclical application of the third electric field and the fourth electric field treats a mood disorder affecting the subject.

In some instances, the method 1200 may include determining, one or more angles that are orthogonal relative to a geometric center of a region of interest, and determining, based on the one or more angles, the first direction.

In some instances, the method 1200 may include determining, based on a location of a tumor in a brain, one or more implantation positions for the first transducer array and the second transducer array within the brain to treat the tumor.

Figure 13:
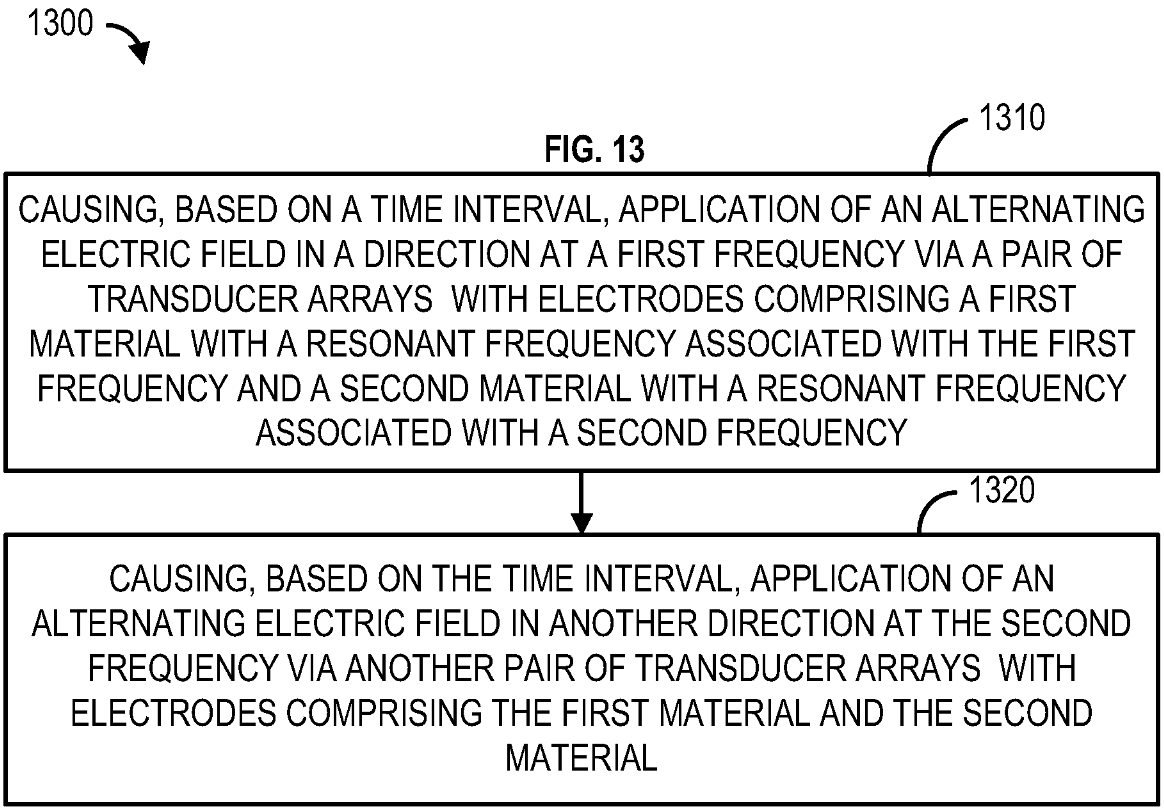
FIG. 13 shows an example method.

In an embodiment, illustrated in FIG. 13, one or more of the apparatus 100, the patient support system 602, the patient modeling application 608, and/any other device/component described herein can be configured to perform a method 1300 comprising, at 1310, causing, based on a time interval, cyclical application of a first electric field in a first direction via a first transducer array comprising a first plurality of electrodes and a second electric field in a second direction, opposite the first direction, via a second transducer array comprising a second plurality of electrodes, wherein the first electric field and the second electric field are at a first frequency, wherein each electrode of the first plurality of electrodes and each electrode of the second plurality of electrodes comprises a first material with a resonant frequency associated with the first frequency and a second material with a resonant frequency associated with a second frequency.

At 1320, causing, based on the time interval, cyclical application of a third electric field in a third direction via a third transducer array comprising a third plurality of electrodes and a fourth electric field in a fourth direction, opposite the third direction, via a fourth transducer array comprising a fourth plurality of electrodes, wherein each electrode of the third plurality of electrodes and each electrode of the fourth plurality of electrodes comprises the first material with the resonant frequency associated with the first frequency and the second material with the resonant frequency associated with the second frequency, and wherein the third electric field and the fourth electric field are at the second frequency.

In some instances, based on the first frequency, the cyclical application of the first electric field and the second electric field treats a tumor within the brain of a subject, and wherein, based on the second frequency, the cyclical application of the third electric field and the fourth electric field treats a mood disorder affecting the subject. In some instances, the first frequency may include a frequency between 50 and 500 kHz, and the first electric field and the second electric field may each include an electric field strength of at least 1 V/cm or electric field strength produced by an amperage supplied to the electrode of 0.5-4.0 mA, and the second frequency may include a frequency of less than 640 Hz. In some instances, the first material may include and/or be ceramic and the second material may include and/or be rubber.

In some instances, the method 1300 may include determining, one or more angles that are orthogonal relative to a geometric center of a region of interest, and determining, based on the one or more angles, the first direction and the third direction.

In some instances, the method 1300 may include determining, based on a location of a tumor in a brain, one or more implantation positions for each of the transducer arrays within the brain to treat the tumor.

In view of the described apparatuses, systems, and methods and variations thereof, hereinbelow are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising: causing cyclical application of a first electric field in a first direction via a first transducer array comprising a first plurality of electrodes and a second electric field in a second direction, opposite the first direction, via a second transducer array comprising a second plurality of electrodes, wherein the first electric field and the second electric field are at a first frequency, wherein each electrode of the first plurality of electrodes and each electrode of the second plurality of electrodes comprises a first material with a resonant frequency associated with the first frequency and a second material with a resonant frequency associated with a second frequency, and causing cyclical application of a third electric field in the first direction via the first plurality of electrodes and a fourth electric field in the second direction, via the second plurality of electrodes, wherein the third electric field and the fourth electric field are at the second frequency.

Embodiment 2: The embodiment as in any one of the preceding embodiments wherein, based on the first frequency, the cyclical application of the first electric field and the second electric field treats a tumor within the brain of a subject, and wherein, based on the second frequency, the cyclical application of the third electric field and the fourth electric field treats a mood disorder affecting the subject.

Embodiment 3: The embodiment as in any one of the preceding embodiments, wherein the first frequency comprises a frequency between 50 and 500 kHz and the first electric field and the second electric field each comprise an electric field strength of at least 1 V/cm or electric field strength produced by current supplied to the electrode of 0.5-4.0 mA, and the second frequency comprises a frequency of less than 640 Hz.

Embodiment 4: The embodiment as in any one of the preceding embodiments, wherein the first material comprises ceramic and the second material comprises rubber.

Embodiment 5: The embodiment as in any one of the preceding embodiments further comprising determining, one or more angles that are orthogonal relative to a geometric center of a region of interest, and determining, based on the one or more angles, the first direction.

Embodiment 6: The embodiment as in any one of the preceding embodiments further comprising determining, based on a location of a tumor in a brain, one or more implantation positions for the first transducer array and the second transducer array within the brain to treat the tumor.

Embodiment 7: A method comprising: causing, based on a time interval, cyclical application of a first electric field in a first direction via a first transducer array comprising a first plurality of electrodes and a second electric field in a second direction, opposite the first direction, via a second transducer array comprising a second plurality of electrodes, wherein the first electric field and the second electric field are at a first frequency, wherein each electrode of the first plurality of electrodes and each electrode of the second plurality of electrodes comprises a first material with a resonant frequency associated with the first frequency and a second material with a resonant frequency associated with a second frequency, and causing, based on the time interval, cyclical application of a third electric field in a third direction via a third transducer array comprising a third plurality of electrodes and a fourth electric field in a fourth direction, opposite the third direction, via a fourth transducer array comprising a fourth plurality of electrodes, wherein each electrode of the third plurality of electrodes and each electrode of the fourth plurality of electrodes comprises the first material with the resonant frequency associated with the first frequency and the second material with the resonant frequency associated with the second frequency, and wherein the third electric field and the fourth electric field are at the second frequency.

Embodiment 8: The embodiment of claim 7, wherein, based on the first frequency, the cyclical application of the first electric field and the second electric field treats a tumor within the brain of a subject, and wherein, based on the second frequency, the cyclical application of the third electric field and the fourth electric field treats a mood disorder affecting the subject.

Embodiment 9: The embodiment as in any one of embodiments 7-8, wherein the first frequency comprises a frequency between 50 and 500 kHz and the first electric field and the second electric field each comprise an electric field strength of at least 1 V/cm or electric field strength produced by amperage supplied to the electrode of 0.5-4.0 mA, and the second frequency comprises a frequency of less than 640 Hz.

Embodiment 10: The embodiment as in any one of the embodiments 7-9, wherein the first material comprises ceramic and the second material comprises rubber.

Embodiment 11: The embodiment as in any one of the embodiments 7-10 further comprising determining, one or more angles that are orthogonal relative to a geometric center of a region of interest, and determining, based on the one or more angles, the first direction and the third direction.

Embodiment 12: The embodiment as in any one of the embodiments 7-11 further comprising determining, based on a location of a tumor in a brain, one or more implantation positions for each of the transducer arrays within the brain to treat the tumor.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for treating a tumor within a brain of a subject, comprising:

providing first and second transducer arrays on a body of the subject, each comprising a plurality of first electrodes comprising a first material and having a first resonant frequency corresponding to a first frequency and a plurality of second electrodes comprising a second material and having a second resonant frequency corresponding to a second frequency different to the first frequency, wherein the first material and the second material are different materials;

causing application of a first electric field at the first frequency via the pluralities of first electrodes of the first and second transducer arrays; and causing application of a second electric field at the second frequency via the pluralities of second electrodes of the first and second transducer arrays, wherein the first frequency comprises a frequency between 50 and 500 kHz, and the second frequency comprises a frequency of less than 640 Hz, and wherein, based on the first frequency, the first electric field treats the tumor, and, based on the second frequency, the second electric field treats a neurological and/or mental condition affecting the subject.

2. The method of claim 1, further comprising:

determining, based on a location of the tumor in the brain of the subject, one or more positions for the first transducer array and the second transducer array on the subject to treat the tumor.

3. The method of claim 1, wherein the first electrodes comprise a ceramic.

4. The method of claim 1, wherein the second electrodes comprise a rubber.

5. The method of claim 1, wherein the first and second electrodes are arranged as concentric pairs.

6. The method of claim 1, further comprising:

providing third and fourth transducer arrays on the body of the subject, each comprising a plurality of third electrodes with the first resonant frequency corresponding to the first frequency and a plurality of fourth electrodes with the second resonant frequency corresponding to the second frequency; and causing cyclical application of the first electric field at the first frequency in a first direction via the pluralities of first electrodes of the first and second transducer arrays and a third electric field at the first frequency in a second direction via the pluralities of third electrodes of the third and fourth transducer arrays.

7. The method of claim 6, wherein the first and second directions are perpendicular.

8. The method of claim 6, wherein the third and fourth electrodes are arranged as concentric pairs.

9. The method of claim 6, further comprising:

causing cyclical application of the second electric field at the second frequency in a third direction via the pluralities of fourth electrodes of the third and fourth transducer arrays and a fourth electric field at the second frequency in a fourth direction via the pluralities of fourth electrodes of the third and fourth transducer arrays.

10. The method of claim 9, wherein the first and third directions are perpendicular to the second and fourth directions.

11. The method of claim 1, further comprising:

causing cyclical application of the second electric field at the second frequency in opposite directions via the second pluralities of electrodes of the first and second transducer arrays.

12. The method of claim 1, wherein, based on the first frequency, the first electric field treats glioblastoma multiforme.

13. The method of claim 1, wherein, based on the second frequency, the second electric field treats one or more of depression, major depressive disorder, anxiety, cognitive decline, addiction, or stroke after-effects.

14. An apparatus, comprising:

first and second transducer arrays configured to be placed on a body of a subject, each comprising a plurality of first electrodes comprising a first material and having a first resonant frequency corresponding to a first frequency and a plurality of second electrodes comprising a second material and having a second resonant frequency corresponding to a second frequency different to the first frequency, wherein the first material and the second material are different materials, wherein the first frequency comprises a frequency between 50 and 500 kHz and the second frequency comprises a frequency of less than 640 Hz, and wherein, based on the first frequency, the first electric field is configured to treat a tumor within a brain of the subject, and, based on the second frequency, the second electric field is configured to treat a neurological and/or mental condition affecting the subject;

an electric field generator;

one or more processors; and memory storing processor-executable instructions that, when executed by the one or more processors, cause the apparatus to at least:

cause application of a first electric field at the first frequency via the pluralities of first electrodes of the first and second transducer arrays; and cause application of a second electric field at the second frequency via the pluralities of second electrodes of the first and second transducer arrays.

* * * * *